United States Patent [19]

McKenzie et al.

[11] Patent Number: 5,084,266
[45] Date of Patent: Jan. 28, 1992

[54] METHOD FOR TUMOR IMAGING UTILIZING A LABELLED TUMOR SPECIFIC ANTIBODY AND A NON-TUMOR REACTIVE ANTIBODY

[75] Inventors: Ian F. C. McKenzie, West Brunswick; Joe J. Tjandra, Kew, both of Australia

[73] Assignee: The University of Melbourne, Parkville, Australia

[21] Appl. No.: 305,539

[22] Filed: Feb. 2, 1989

[30] Foreign Application Priority Data

Feb. 3, 1988 [AU] Australia ............................... 6558/88

[51] Int. Cl.$^5$ ..................... G01N 31/00; G01N 24/00; G01N 33/53
[52] U.S. Cl. .......................................... 424/9; 424/1.1; 424/4; 436/173; 436/547; 436/548; 436/806
[58] Field of Search ................ 424/9, 1.1, 4; 436/173, 436/548, 547, 806; 128/654, 653 R, 653 CA

[56] References Cited

U.S. PATENT DOCUMENTS

| | | | |
|---|---|---|---|
| 4,331,647 | 5/1982 | Goldenberg | 424/1.1 |
| 4,444,744 | 4/1984 | Goldenberg | 424/1.1 |
| 4,478,815 | 10/1984 | Burchiel et al. | 424/1.1 |
| 4,624,846 | 11/1986 | Goldenberg | 424/1.1 |
| 4,735,210 | 4/1988 | Goldenberg | 128/654 |
| 4,938,948 | 7/1990 | Ring et al. | 424/9 |

*Primary Examiner*—Glennon H. Hollrah
*Assistant Examiner*—Gary E. Hollinden
*Attorney, Agent, or Firm*—Scully, Scott Murphy & Presser

[57] ABSTRACT

A method for identifying and/or determining the location of a tumor which produces or is associated with a cytoplasmic, intra-cellular or cell surface marker substance, is disclosed, which comprises the steps of:

(a) injecting a human or animal subject with tumor specific antibody or a fragment thereof specific for the marker and labelled with a radioactive isotope of an element or a paramagnetic conjugate; and an irrelevant (non-tumor reactive) antibody which has been labelled with a non-radioactive isotope of the same or other element, or a non-paramagnetic conjugate; and (b) after a period of time sufficient for selective binding of the labelled tumor specific antibody to the tumor scanning the human or animal subject with a detector to locate the site or sites of uptake of labelled antibody or fragments thereof.

Imaging compositions are also described.

24 Claims, No Drawings

METHOD FOR TUMOR IMAGING UTILIZING A LABELLED TUMOR SPECIFIC ANTIBODY AND A NON-TUMOR REACTIVE ANTIBODY

The present invention relates to tumour identification and localisation utilizing antibodies specific for tumour antigens. [Note: References are collected at the end of the specification.]

Since the advent of monoclonal antibodies with a preferential activity for cancer tissue, radiolabelled antibodies have been used in radioimmunodetection of cancer and its metastases. Administration of radiolabelled antibodies combined with nuclear imaging (hereinafter referred to as immunoscintigraphy) has allowed detection of a wide range of tumours in different sites. Imaging procedures using intravenously administered radiolabelled antibodies are limited by background radioactivity in the blood pool and extravascular spaces and, furthermore, antibodies may be catabolised before reaching their target, resulting in only a very small tumour uptake.

The concept of immunoscintigraphy has been extended to using subcutaneously injected radiolabelled tumour-associated antibodies to delineate metastatic deposits in regional lymph nodes. These earlier studies have shown that non-specific uptake by normal lymph glands and other tissues has been a major problem which severely hampers the effectiveness of the imaging techniques.

It has previously been proposed to reduce non-specific or non-target antibody binding, and thus enhance the resolution of tumour imaging, by the following techniques:

(i)

Injecting patients intravenously with an antibody preparation containing tumour specific antibody, and an excess of unlabelled antibody.

This technique has been largely unsatisfactory in reducing non-specific antibody binding. As tumours are bathed in extracelluar fluids containing antibodies and large amounts of other proteins such as albumin, it is not surprising that the administration of additional antibody is largely ineffective in reducing background.

(ii)

The administration of tumour specific antibody labelled with a radionuclide, and labelled human serum albumin or a second radionuclide (usually $^{99m}$Tc) capable of imaging normal tissue. Specific binding of tumour specific antibody is detected by subtracting the signal produced by the second radionuclide.

The disadvantage with this approach is that a patient is exposed to increased levels of radiation, with attendant side affects. Further, independent detection devices may be required to detect the signal from different radionuclides, thus making this procedure costly and cumbersome. In addition, the isotopes used in substraction (e.g. technetium) do not distribute in exactly the same way as normal IgG.

(iii)

Injecting a subject intravenously with a tumour specific antibody labelled with a radionuclide, and, after sufficent time to permit antibody-tumour binding injecting the patient with a second non-labelled antibody or fragment thereof, specific against the tumour specific antibody. The second antibody clears non-bound antibody from the circulation thus improving the resolution of tumour imaging. Such a technique is described in U.S. Pat. No. 4,624,846.

The above technique has the disadvantage that binding of the second antibody to the tumour specific antibody results in the formation of large antibody aggregates, which may cause immune complex disease (as antibody aggregates are much more immunogenic than monomeric molecules), damage to the reticuloendothelial system, and kidney overload, with its associated complications.

If the tissue distribution of the tumour specific antibody, and the second antibody is different, a poor result will be obtained on imaging. Additionally, this technique is not suitable for subcutaneous tumour imaging, and in particular, the imaging of tumours associated with the lymphatic system. Labelled tumour specific antibody would be taken up specifically by tumours, and non-specifically by normal lymph nodes and other tissues. Such antibody would not be accessible for clearance by a second anti-tumour antibody.

The present invention is based on the surprising finding that the background non-specific antibody binding of isotopically labelled tumour specific antibodies normally associated with tumour imaging, is significantly reduced if a patient is injected with both a tumour specific antibody labelled with a radioisotope of an element and an antibody which is not specifically tumour-reactive and which is labelled with a non-radioactive isotope of the same or other element. The identification and location of tumours is thus facilitated.

According to the present invention, there is provided a method for identifying and/or determining the location of a tumour which produces or is associated with a cytoplasmic, intra-cellular or cell surface marker substance, the method comprising the steps of:

(a) injecting a human or animal subject with tumour specific antibody or a fragment thereof specific for the marker and labelled with a radioactive isotope of an element or a paramagnetic conjugate, and an irrelevant (non-tumour reactive) antibody which has been labelled with a non-radioactive isotope of the same or other element, or a non-paramagenetic conjugate; and (b) after a period of time sufficient for selective binding of the labelled tumour specific antibody to the tumour scanning the human or animal subject with a detector to locate the site or sites of uptake of labelled antibody or fragments thereof.

The present invention has particularly utility in the identification and location of subcutaneous tumours, and in particular breast cancer, and associated lymph node metastases. Currently the best predictor of occult metastases is the involvement of axillary lymph nodes by the tumour, the detection of which involves axilliary dissection with its associated morbidity. Clinical assessment of axillae is notoriously unreliable, and of patients with breast cancer who have no palpable lymph nodes in the axillae, about one third have histological evidence of lymph node invasion. The detection of lymph node metastases will be greatly facilitated by the present invention which avoids the complications of surgery and axillary dissection. It is to be understood however, that the invention is not limited to such specific applications.

Tumour associated markers may be associated with the cytoplasmic, intracellular, or cell-surface regions of tumour cells. Advantageously, the tumour associated markers are cell-surface antigens. Tumour associated markers are generally associated only with tumours and are not associated with other non-tumour tissues such as muscle, fat, blood vessels and erythrocytes. Small amounts of reactivity with non-tumour tissue may however be tolerated where this reactivity is weak compared with tumour reactivity.

Irrelevant antibody is generally non-tumour reactive. However, small amounts of tumour reactivity may be tolerated.

Human or animal subjects may be injected intravenously, intraperitonelly or subcutaneously with antibody or antibody fragments. Advantageously, antibodies are administered by subcutaneous injection in the fields of the lymphatic drainage to detect lymph node metastases. In relation to breast cancer identification, antibodies may be injected into the arm, chest or breast itself.

Antibodies employed may be monoclonal or polyclonal or Fab, (Fab)$_2$ portions thereof. Antibodies may be of mouse, human, hamster horse, goat, rat, rabbit or other animal origin. Antibodies may have one or more heavy or light chains from different species. Where monoclonal antibodies are employed, they may be of any isotype. The tumour specific antibody and irrelevant antibody may be of the same or different isotype. Advantageously, antibodies of the same isotype are preferred. Antibodies of the IgG or IgM isotype are preferred. Polyclonal or monoclonal antibodies and fragments thereof may be prepared by methods well known to persons skilled in the art, such as those described in Goding (1986).

Isotopically or paramagnetically labelled antibody or antibody fragments specific for a tumour marker (hereinafter referred to as "tumour specific antibody") and non-tumour antibody labelled with a non radioactive isotope or non paramagnetic element (hereinafter referred to as "cold labelled antibody") may be administered to a patient at the same time or substantially at the same time (within an interval of a few minutes). Alternatively, the cold labelled antibody preparation may be administered approximately up to five hours before administration of the tumour specific antibody.

The molar ratios of tumour specific antibody to cold labelled antibody may vary considerably. Generally, the cold labelled antibody is in considerable molar excess, such as two to twenty fold excess.

Antibodies or fragments thereof may be labelled with radioactive or non-radioactive isotopes of an element according to methods well known to persons skilled in the art, and described for example in Goding (1986). Radioisotopes of iodine (e.g. $^{131}$I, $^{125}$I, $^{123}$I) indium (e.g. $^{111}$In) and technecium ($^{99m}$Tc) may be employed in the invention, as may the non-radioactive isotopes of these elements. The present invention is not limited to the use of the aforementioned radioisotopes. Other radioisotopes emitting a detectable signal may be employed. Preferably, the tumour specific antibody and irrelevant antibody are labelled with the same element, that is, the tumour specific antibody is labelled with a radioactive isotope of a particular element, and the irrelevant antibody is labelled with a non-radioactive form of the same element.

Suitable paramagnetic labels which may be employed in the invention include atoms or ions that slightly increase a magnetic field, having an odd number of electrons and a partially filled inner shell, such as found in transition elements, rare earth elements and those of the actinide series. Such magnetic labels may include manganese (II), copper (II) and cobalt (II). Other suitable paramagnetic labels are described in G.N. La Mar et al, (1973) which is incorporated herein by reference.

In the case of metal ions, methods of attachments are similar to those previously discussed for radionucleotides. Methods for introducing paramagnetic labels into molecules are disclosed in Paik et al (1982).

Selective binding of a tumour-specific antibody to tumour is generally allowed to proceed for a period of about one hour to four days before tumour imaging is carried out. Advantageously, the time period is from 12 to 36 hours, and preferably from 16 to 24 hours.

Tumour imaging is carried out utilizing a device or detector capable of detecting radionuclide emissions such as a gamma scintillation counter. Where paramagnetic labelling is used, a NMR (Nuclear Magnetic Resonance) spectrometer may be used (Mansfield and Morris 1983).

The immunoscintigraphy method of the present invention is safe and easy to perform. The non-specific uptake of radiolabelled antibody by normal lymph nodes is reduced with the addition of the second cold labelled antibody, resulting in greater differential uptake between malignant and normal lymph nodes with improved tumour detection compared with previous methods.

In accordance with another aspect of the present invention, there is provided a tumour imaging composition which comprises:

(i) a tumour specific antibody or a fragment thereof labelled with a radioactive isotope of an element or a paramagnetic conjugate; and (ii) a non-tumour reactive antibody labelled with a non-radioactive isotope of the same or other element, or a non-paramagnetic conjugate; in association with a pharmaceutically acceptable carrier or excipient.

Pharmaceutically acceptable carriers or excipients include sterile water, physiological saline, albumin and other proteinaceous carriers, and carbohydrate based solutions such as mannitol or dextrose. Other examples of pharmaceutically acceptable carriers or excipients are detailed in Remington's Pharmaceutical Sciences, 16th Ed. Mach Publishing Co., edited by Osol et al., which is hereby incorporated by reference.

ABBREVIATIONS

MoAb—monoclonal antibody
PBS—phosphate buffered saline;

The present invention will now be described, by way of example only, with reference to the following non-limiting examples.

EXAMPLE 1

Materials and Methods

Monoclonal Antibodies (MoAbs)

The monoclonal antibody used was 17.1 (IgG2a). The 17.1 MoAb is a mouse IgG2a immunoglobulin raised by immunising inbred Biozzi mice with the MCF-7 breast cell line (Thompson et al 1983). It reacts with most breast cell lines and breast carcinomas but has no reaction with other tissues of relevance to this study (e.g. muscle, fat, blood vessel, erythrocytes). The Ly-2.1 MoAb was reactive with the murine Ly-2.1 specificity but not with human breast cancer (Hogarth et al 1982). Both 17.1 and Ly-2.1 MoAbs were isolated from ascitic fluid by precipitation with 40% ammonium sulphate, dissolution in PBS and dialysis with the same buffer. Prior to adsorption onto Protein A-Sepharose (Pharmacia Inc., Piscataway, N.J.), the column was washed extensively with PBS (isotonic saline bufered with sodium phosphate and disodium phosphate to a pH of 7.3) and the immunoglobulin eluted with 0.2M glycine-HCl (pH 2.8). After neutralization, MoAbs were dialysed against PBS, aliquoted and stored at −70° C.

Antibody activity was determined by rosetting with sheep anti-mouse immunoglobulin (Parish, C.R. 1978) and in the case of 17.1 also by immunoperoxidase methods on snap-frozen sections of fresh breast cancer (Thompson et al 1983). The prepared antibodies were retested for activity after all procedures, filtered through a 0.22 μm Millex-GV filter (Millipore, Bedford, Ann Harbor, Michigan, USA) and batch tested for pyrogens and sterility before and after radiolabelling (Pharmacology Department, Melbourne University and Sigma Pharmaceuticals, Clayton, Vic., Australia).

Iodination of Monoclonal Antibodies

The 17.1 antibody (400 μg) was labelled with 2 μCi of $^{131}$I (200 μCi/ml, Amersham Inc., UK) to a specific activity of 1 μCi of $^{131}$I per mg of 17.1 antibody using the enzymobead reagent (Morrison) and the final radioiodinated antibody was suspended in a 1% human serum albumin solution (HSA; Commonwealth Serum Laboratories, Melbourne, Australia). The murine MoAb Ly2.1 (2 mg) was labelled with cold sodium iodide (non-radioactive NaI) by means of the chloramine T method (Greenwood). Iodinated antibody was separated from free iodine on a Sephadex G-25 column (PD10, Pharmacia, Sweden) which had previously been equilibrated with 3 ml of 25% human serum albumin and 30 mls of sterile normal saline (Travenol Laboratories, NSW, Australia). The radioactivity of the iodinated antibody was measured in both a gamma counter (LKB Wallac 1260, Finland) and radioisotope calibrator (Capintec CRC-2Ni capintec, New York, USA), and the radiolabelled protein peak pooled. The sample was then centrifuged at 100,000×g for 60 minutes to remove aggregated proteins. Finally, the radiolabelled antibody was filtered through a 0.22 μm Millipore filter in a sterile laminar-flow hood, before clinical use.

The antibody 17.1 (200 μg) was also labelled with lmCi of $^{131}$I (200 μCi/ml, Amersham Inc. UK) to a specific activity of lmCi of $^{131}$I per mg of 17.1 antibody using the chloramine T (Greenwood 1963), iodobead (Markwell 1982) or enzymobead method (Morrison 1970) to compare the effect on antibody activity by different iodination methods (see Example 2).

Patient Section

Thirty-six patients with histologically or cytologically proven breast cancer were studied. All patients except four (Stage IV, 2 patients; benign breast disease, 2 patients) had Stage I or II breast cancer using the standard UICC classification (American Joint Committee on Staging). The clinical assessment of axillary lymph node status was performed independently by two experienced breast surgeons. All patients with stage I or II breast cancer had axillary dissection either as part of Patey mastectomy, or in addition to partial mastectomy. Two patients with a benign breast lump (sclerosing adenosis) was studied: initial fine needle aspiration cytology (FNAC) suggested the presence of malignant cells but subsequent excision biopsy failed to find any malignancy. Two patients had breast cancer proven by fine needle aspiration cytology but subsequently were found to have Stage IV breast cancer with bone metastases; neither had axillary dissection but they both had malignant axillary lymph nodes on clinical examination. Of the patients studied, 11% (4/36) received radioiodinated 17.1 injected subcutaneously into the arms, 3% (1/36) had periareolar injection into the breast of radioiodinated 17.1, 81% (29/36) received radioiodinated 17.1 (reactive with breast cancer) together with cold labelled Ly2.1 (non-reactive with breast cancer) administered subcutaneously into both arms, and 8% (3/36) received radioiodinated 17.1 together with unlabelled Ly2.1 injected subcutaneously into both arms. One patient who received radioiodinated 17.1 alone in her arms had daily scans performed up the fourth day after injection. To inhibit thyroid uptake of radioactive iodine, each patient received potassium iodide (5 ml of 16.54% w/v) and sodium perchlorate (400 mg) orally, one hour before the subcutaneous injection of radioiodinated monoclonal antibody. The potassium iodide was continued for 5 days after the injection of $^{131}$I.

Blood samples were obtained from all patients immediately before, and 6 weeks after injection of radioiodinated MoAbs for determining human anti-mouse antibody (HAMA) response.

Imaging

Scintillation-camera images were recorded 16–18 hours after injection of the radiolabelled antibody. Anterior axillary and upper body scans were recorded with a Toshiba GC A402 gamma camera using a high-energy collimator and computerised acquisition with an informatek Simis 4 computer (Informatek, Sydney, Australia). A window setting of 360 KeV with a 20% window was used. Images were obtained over a period of 600 seconds and then digitally recorded into a matrix of 128×128 words.

Regions of interest on the images were defined by manual drawing over the axillary lymph node regions on both sides using anatomical landmarks as well as adjacent background and the heart. Definition of anatomical regions was performed by 2 independent investigators and has been found to be remarkably reproducible. The fraction of radiolabelled antibody localised in the axillary nodes (F) was estimated by measurement of nodal uptake (N) with the gamma camera, and comparison with uptake in the other regions of interest and the amount of radiolabelled antibody injected (I). Nodal uptake was adjusted for background activity (B), camera response and attenuation through the anterior axillary fold using an attentuation factor (A) calculated using a known source placed in the axilla. The following formulae were used:

$$F(\%) = (N_1/I) \times 100 \qquad \text{Formula 1}$$

$$N_2 = \left| n - \frac{bPn}{P_b} \times \frac{A}{e^{-\mu x}} \right| \qquad \text{Formula 2}$$

$$N_2(cpm) = N_1(\mu Ci) \times \text{camera sensitivity} \qquad \text{Formula 3}$$

Where
F = Fraction of antibody localised in the nodes.
N = nodal uptake ($N_1$ in μCi, $N_2$ in cpm)

n = total gamma camera counts (cpm) over lymph node regions
I = actual injected dose (μCi)
b = background activity (cpm)
$P_n$ number of pixels in region of intest (lymph node region)
$P_b$ = number of pixels in background
A = attenuation factor (1/1.37)
$e^{-\mu x}$ = correlation factor for isotope decay = 0.94 for $^{131}$I at 18 hrs Camera sensitivity was determined by counting the amount of counts per minute (cpm) with a known amount (1 μCi) of $^{131}$I.

Scans were reported as positive, and therefore indicative of lymph node metastases, if the number of countes per pixel in the axilla on the tumour side exceeded the normal side by a ratio greater than 1.5:1, after adjustment for background activity as indicated above.

Analysis of Excised Lymph Nodes and Breast Cancer tissue

In most instances patients had surgery 36–40 hrs after the injection of radio-iodinated antibody. At surgery the nodes were removed in a tissue block and pinned onto a foam board to facilitate orientation. After formalin fixation at room temperature overnight, each node was dissected free of fat and in some cases gamma camera images, radioactive count and the weights of individual nodes were obtained.

Each node was processed, stained and 6 μm sections were examined histologically for tumour. To assess binding of the antibody to any tumour cells present in the lymph nodes, immunoperoxidase staining of snap-frozen sections from some patients was performed using both the indirect two-stage and a one stage direct application of rabbit anti-mouse-peroxidase conjugate (Thompson, C. H., Epenetos et al). In addition, fresh breast cancer tissue was also obtained from some patients, snap-frozen and tested for its reactivity with 17.1 antibody by immunoperoxidase staining. A non-reactive, negative control was processed for each lymph node section by incubating with an anti-human colon MoAb 30.6, as the primary antibody. The sections were then assessed by light microscopy to estimate the percentage of carcinoma cells stained with the antibody and the result expressed semi-quantitatively as 0–4 according to whether there was no staining (0), up to 25% (1), 26–50% (2), 51–75% (3) or more than 75% (4) of cells stained.

EXAMPLE 2

Comparison of Radioiodination Methods

To select the best radioiodination method, a comparison was made of the yield of incorporation of the 17.1 antibody after radioiodination with Chloramine T, iodobead and enzymobead methods (Table 1). Using the rosetting assay and immunoperoxidase staining independently, the Chloramine T method resulted in a greater loss of immunoreactivity than either the iodobead or enzymobead method as assessed by the titre of antibody and percentage of rosette forming cells and by the staining score on immunoperoxidase. Immunoreactivity after labelling was also tested by radioimmunoassay (RIA) for 17.1 against a breast cancer cell line. There was a 25-fold difference between the reaction of $^{131}$I-labelled 17.1 on the breast carcinoma cell line (T47D-17.1+) compared to melanoma cell line (COLO 239-17.1−), and labelled antibody competed well with unlabelled antibody for antigen binding. The enzymobead method resulted in minimal loss of reactivity, while chloramine T method resulted in greatest loss of reactivity. The enzymobead method was, therefore, used as the method of choice for labelling 17.1.

EXAMPLE 3

Immunolymphoscintigraphy (i) 131I-17.1 (400 μg) and cold Labelled Ly-2.1 (2 mg): Arm Injection Twenty-six patients (Table 2) received radioiodinated 17.1 antibody (reactive with breast cancer) with a specific activity of 1mCi $^{131}$I per mg of 17.1 (by enzymobead method) together with cold labelled Ly2.1 (non-reactive with breast cancer) injected subcutaneously into both arms just above the ante-cubital fossae. The Chloramine T method was used to iodinate Ly2.1 antibody to maximally produce damaged moAb. Correct prediction of lymph node status was achieved in 92% (24/26) patients). Fourteen of the 26 patients had histologically proven axillary lymph node metastases and 13/14 (93%) patients were detected by the scan, while 12/26 patients did not have lymph node metastases and a negative scan was obtained in 11/12 (92%) of patients.

Several representative examples of patients in this study are described in more detail below.

Patient WT had right breast cancer and clinically non-involved axillary lymph nodes. She underwent right Patey mastectomy and a single focus of micrometastases was identified in 1 of the 12 axillary lymph nodes recovered on histology. The preoperative immunolymphoscintigraphy showed an increased localisation of $^{131}$I-17.1 in the right axillary lymph node region with a ratio between axilla of interest (R) and contralateral axilla (L) of 1.5:1.

Patients KS clinically was considered to have axillary lymph node metastases but scanning showed equal uptake of $^{131}$I-17.1 in both axillae with ratio of background substracted count density of 1:1 between the 2 axillae. Histology of the 14 lymph nodes recovered showed reactive hyperplasia only with no metastases. The immunoperoxidase staining of regional lymph nodes with 17.1 antibody also did not identify any tumour deposits.

(ii) $^{131}$I-17.1 (1 mg) and Cold Labelled Ly-2.1 (2 mg): Arm Injection

Three patients (Table 2) received a higher dose of specific MoAb (17.1 1 mg) while maintaining the same amount of $^{131}$I (2 μCi) to a specific activity of 0.5mCi of $^{131}$I per mg of antibody. The same amount cold iodine-labelled Ly-2.1 MoAb was given. Correct prediction of lymph nodes status was achieved in 3/3 patients including 1 patient who had a benign breast lump but the amount of radioactive uptake in either axilla is less with a poor quality image.

Tables 3 and 4 summarise the results and statistical analysis of preoperative clinical assessment and axillary immunolymphoscintigraphy in 26 patients who received $^{131}$I-17.1 (400 μg) and cold labelled Ly-2.1 (2 μg). This new method of immunoscintigraphy with the use of two antibodies is much more sensitive (93%) and specific (92%) than preoperative clinical assessment (57% sensitivity, 58% specificity) but still not quite as accurate as axillary dissection and histological assessment which is the standard against which it is compared. Overall accuracy of this new method of immunoscintigraphy (92%) was undoubtedly superior to preoperative clinical assessment (58%).

Patients tolerated the immuno lymphoscintigraphy procedures easily and there were no allergic reactions or sepsis locally or generalised. One patient who had chronic asthma and was receiving steroids, had an exacerbation of her asthma which was easily controlled by increasing the dose of the steroid. Human anti-mouse antibody (HAMA) response was detected in the serum of only 1 patient at 4 weeks after injection.

Table 5 shows the amount of radioactivity uptake in metastatic lymph nodes, normal lymph nodes and axillary fat in 2 patients, one of whom (Patient 1) had $^{131}$I-17.1 (400 μg) alone, the other (Patient 2) had $^{131}$I-17.1 (400 μg) and cold labelled Ly-2.1 (2 mg). Correction was made to account for the physical half-life of $^{131}$I to obtain a relative count with regard to the injected amount. The localization index refers to the ratio of radiolabelled antibody present in the ratio counted. Only 2 axillary specimens were examined by the method, but the localization index of radioactivity in the involved nodes were higher than the normal nodes in the patient who received $^{131}$I-17.1 and cold labelled Ly-2.1 than the patient who had $^{131}$I-17.1 alone. The background counts from the surrounding fat were low.

(iii) $^{131}$I-17-1 (400 μg) and Unlabelled Ly2.1 (2 mg): Arm Injection

Three patients (Table 2) were injected with radioiodinated 17.1 (400 μg) together with unlabelled Ly2.1 (2 mg). Incorrect prediction of lymph node metastases were obtained in all three patients.

(iv) $^{131}$I-17.1 (400 μg): Arm Injection

Four patients (Table 2) received radioiodinated 17.1 alone. One of the four patients had sclerosing adenosis, a benign condition, while the other three patients had breast cancer. Correct prediction of lymph node metastases was obtained in 1/4 patients. In 2/4 patients, the uptake of radioiodinated 17.1 was, in fact, higher in the normal axilla. The fourth patient, with advanced breast cancer (Stage IV) and malignant left axillary lymph nodes on clinical examination, was also injected with $^{131}$I-labelled 17.1 (400 μg) into both arms subcutaneously. Serial scans were obtained at 16 hrs, 40 hrs and 64 hrs after injection and showed equal uptake in both axillae. The differential uptake between abnormal and normal axillae did not change with time and appears to be optimal at 16 hrs after injection.

In a further experiment, three patients received radioiodinated Ly2.1 alone. Two patients without axillary lymph node metastases received $^{131}$I-Ly2.1 with a specific activity of 0.25 mCi/mg (total amount of antibody injected=2 mg) and one patient with right axillary lymph node metastases received $^{131}$I-Ly2.1 with a specific activity of 1 mCi/mg (total amount of Ly2.1 injected=400 μg). In each patient, the amount of radioactive uptake between the two axillae was the same, even in the presence of axillary lymph node metastases. It appears from this study that the uptake of radioiodinated Ly2.1 is the same between node positive and node negative axillae suggesting that the blocking of non-specific uptake was independent of the size of the lymph nodes or the presence of lymph node metastases.

EXAMPLE 4

Correlation with Immunoperoxidase Staining

To assess the reactivity of the breast cancer with 17.1 and the binding of 17.1 to any tumour cells present in the axillary lymph nodes, immunoperxidase staining of snap-frozen sections using both the indirect two-stage (primary breast cancer and lymph nodes) and a one-stage (lymph node) direct application of rabbit anti-mouse-peroxidase conjugate was performed. Fresh sections were obtained from 10 patients, all of whom had $^{131}$I-17.1 and cold labelled Ly-2.1 and 6/10 patients had lymph node metastases. Five out of these six patients had primary breast cancer and lymph node metastases which reacted strongly with 17.1 (staining score 3–4) These five patients had strongly positive scans. On the other hand, 1/6 patients had primary breast cancer and lymph node metastases which reacted only poorly (staining score 1) with 17.1 and the immunoscintigraphy failed to detect the lymph node metastases in this case, suggesting that failure of the method to localise lymph node metastases may be contributed, in part, by the poor reactivity of the 17.1 MoAb with the particular tumour.

In these experiments, antibodies of the IgG subclass were used. Studies we have performed with antibodies of different subclass, show that antibody subclass is of little importance.

It has previously been established that 17.1 reacted with only 90% of fresh breast cancer sections examined (unpublished observations) presumably due to the phenomenon of tumour heterogeneity both within and between different tumour deposits. As shown in a patient whose breast cancer only reacted poorly with 17.1, the immunoscintigraphic scan failed to identify the lymph node metastases. This may account for false negative rate in example 3(i) of this study (7% or 1/4), but this has yet to be proven.

The mechanism of non-specific antibody uptake by normal lymph nodes and the mechanisms of action of the second cold labelled antibody are not clear at this time. The improvement in results obtained with the addition of a second antibody in excess may be due to the competition for non-specific binding to normal lymph nodes.

REFERENCES

American Joint Committee on Staging, Manual for Staging of Cancer, 2nd Edition, Philadelphia, Lippinsott (1983).

Greenwood, F. C., Innter, W. M. and Glover, J. S., Biochem. J. 1063; 89: 114–123.

Goding, J. W., Monoclonal Antibodies: Principles and Practice, 2nd Edition, Academic Press (1986).

Hogarth, P. M., Henning, M. M. and McKenzie, I. F. C., Immunology; 46: 125–144 (1982).

La Mar, G. N., NMR of Paramagnetic Molecules, Principles and Applications, Academic Press, New York (1973).

Mansfield, P., and Morris, P. G., Advances in Magnetic Resonance (NMR) Imaging, C. L. Partain et al., eds. W. B. Saunders Co. (1983).

Markwell, M. A. K., Annals Biochem.; 125: 472–432 (1982).

Morrison, M. and Boyse, C. S., Biochemistry; 9: 2995–3000.

Paik, S., J. Nucl. Med.; 23: 37 (1982).

Parish, G. R. and McKenzie, I. F. C., J. Immunol. Methods; 20: 173-183 (1978).

Thompson, C. H., Jones, S. L., Whitehead, R. H. et al., J. Natl. Cancer, Inst.; 70: 409-419 (1983).

TABLE 1

Comparison of Three Methods of Iodination on the Activity of 17.1 MoAb by (A) Rosetting Assay and (B) Immunoperoxidase[a]

A

| Technique | % Incorporation | Antibody Titre (% RFC)[b] |
|---|---|---|
| Chloramine T | 82 | 1/5,000 (90) |
| Iodobead | 78 | 1/5,000 (90) |
| Enzymobead | 81 | 1/20,000 (90) |
| Unlabelled Control | — | 1/100,000 (90) |

B

| Technique | Staining Density[c] (and % of carcinoma cells stained) at different MoAb dilutions | | | | | |
|---|---|---|---|---|---|---|
| | $1/10^2$ | $1/10^3$ | $1/10^4$ | $1/5 \times 10^4$ | $1/7 \times 10^4$ | $1/10^5$ |
| Chloramine T | 4 | 4 | 3 | 2 | 1 | 0 |
| Iodobead | 4 | 4 | 3 | 2 | 1 | 0 |
| Enzymobead | 4 | 4 | 4 | 3 | 2 | 0 |
| Unlabelled Control | 4 | 4 | 4 | 3 | 2 | 1 |

[a]All tissues were obtained fresh, immediately snap-frozen, and stored at −70° C.
[b]RFC = rosette forming cells.
[c]Staining score was graded as no stain (0), <25% (1), 26-50% (20, 51-75% (3), >75% (4) of carcinoma cells stained.

TABLE 2

| Method | | Number of Patients |
|---|---|---|
| 1. | $^{131}$I-17.1 (400 μg) + cold labelled Ly-2.1 (2 mg): Arm Injection | 26 |
| 2. | $^{131}$I-17.1 (1 mg) + cold iodine labelled Ly-2.1 (2 mg): Arm Injection | 3 |
| 3. | $^{131}$I-17.1 (400 μg) + unlabelled Ly-2.1 (2 mg): Arm Injection | 3 |
| 4. | $^{131}$I-17.1 (400 μg): Arm Injection | 4 |

TABLE 3

Comparison of Immunolymphoscintigraphy Using 131 I-17.1 MoAb (400 μg) and Cold Iodine Labelled (Blocking) ly2.1 MoAb with Clinical and Pathological Assessment of the Axillae in 26 Patients with Breast Cancer

| | Pathological Node +ve | Assessment[a] Node −ve |
|---|---|---|
| Scan Result[b] | | |
| +ve | 13 | 1 |
| −ve | 1 | 11 |
| Clinical Assessment | | |
| +ve | 8 | 5 |
| −ve | 6 | 7 |

[a]Node +ve implies ≧ nodal metastases
Node −ve implies no nodal metastases
[b]Node +ve = palpable axillary lymph nodes felt to contain tumour deposits.
Node −ve = nodes not palpable, or if palpable, felt not to contain tumour deposits.

TABLE 4

Comparison of Immunolymphoscintigraphy and Clinical Examination in Predicting Axillary Lymph Node Metastases

| Parameter[a] | Immunolympho scintigraphy | Clinical Examinations | Immunolymphoscintigraphy + Clinical Examination |
|---|---|---|---|
| Sensitivity | 93% | 57% | 100% |
| Specificity | 92% | 58% | 50% |
| Accuracy | 92% | 58% | 77% |

[a]Sensitivity = $\frac{TP}{TP + FN}$
Specificity = $\frac{TN}{TN + FP}$
Accuracy = $\frac{TP + TN}{\text{Total No. of patients tested}}$
TP = True Positive;
TN = True Negative;
FP = False Positive;
FN = False Negative

TABLE 5

Concentration (% dose/gm Tissue) of Specific MoAb in Different Tissues

| | $^{131}$I-IgG; Mean | $^{131}$I-IgG + Cold IgG* Mean |
|---|---|---|
| Metastatic LN | $6.4 \times 10^{-2}$ | $1.6 \times 10^{-1}$ |
| Normal LN | $4.2 \times 10^{-2}$ | $9.2 \times 10^{-3}$ |
| Axillary Fat | $2.0 \times 10^{-4}$ | $4.1 \times 10^{-4}$ |

We claim:

1. A method for identifying and/or determining the location of a tumor which produces or is associated with a cytoplasmic, intra-cellular or cell surface marker substance, the method comprising the steps of:
   (a) injecting a human or animal subject with tumor specific antibody or a fragment thereof specific for the marker and labelled with a radioactive isotope of an element, and an irrelevant (non-tumor reactive) antibody which has been labelled with a non-radioactive isotope of the same or other element; and
   (b) after a period of time sufficient for selective binding of the labelled tumor specific antibody to the tumor, scanning the human or animal subject with a detector to locate the site or sites of uptake of labelled antibody or fragments thereof.

2. A method according to claim 1, wherein the tumour specific antibody is labelled with a radioactive isotope selected from the group consisting of a radioactive isotope of iodine, indium and technecium.

3. A method according to claim 1 wherein the specific antibody and irrelevant antibody are of the same isotype.

4. A method according to claim 1, wherein the tumour specific antibody and irrelevant antibody are both monoclonal antibodies.

5. A method according to claim 1, wherein the human or animal subject is injected subcutaneously with the tumour specific antibody and irrelevant antibody.

6. A method according to claim 1, wherein the tumour specific antibody and irrelevant antibody are administered at the same or substantially the same time.

7. A method according to claim 1, wherein the irrelevant antibody is administered up to five hours before administration of the tumour specific antibody.

8. An imaging composition, characterized in that it comprises;
   (i) a tumour specific antibody or a fragment thereof labelled with a radioactive isotope of an element, and
   (ii) a non-tumour reactive antibody labelled with a non-radioactive isotope of the same or other element; in association with a pharmaceutically acceptable carrier or excipient.

9. An imaging composition according to claim 8, wherein the tumour specific antibody is labelled with a radioactive isotope selected from the group consisting of a radioactive isotope of iodine, indium and technecium.

10. An imaging composition according to claim 8, wherein the specific antibody and irrelevant antibody are of the same isotype.

11. An imaging composition according to claim 8, wherein the tumour specific antibody and irrelevant antibody are both monoclonal antibodies.

12. An imaging composition according to claim 8, wherein the tumour specific antibody is 17.1 and the non-tumour reactive antibody is Ly 2.1.

13. A method for identifying and/or determining the location of a tumour which produces or is associated with a cytoplasmic, intra-cellular or cell surface marker substance, the method comprising the steps or:
   (a) injecting a human or animal subject with tumour specific antibody or a fragment thereof specific for the marker and labelled with a paramagnetic element; and an irrelevant (non-tumour reactive) antibody which has been labelled with a non-paramagenetic element and
   (b) after a period of time sufficient for selective binding of the labelled tumour specific antibody to the tumour, scanning the human or animal subject with a detector to locate the site or sites of uptake of labelled antibody or fragments thereof.

14. A method according to claim 13, wherein the paramagnetic element is selected from the group consisting of manganese (II), copper (II) and cobalt (II).

15. A method according to claim 13, wherein the specific antibody and irrelevant antibody are of the same isotype.

16. A method according to claim 14, wherein the tumour specific antibody and irrelevant antibody both comprise IgG, IgM or fragments thereof.

17. A method according to claim 13, wherein the tumour specific antibody and irrelevant antibody are both monoclonal antibodies.

18. A method according to claim 13, wherein the human or animal subject is injected subcutaneously with the tumour specific antibody and irrelevant antibody.

19. A method according to claim 13, wherein the tumour specific antibody and irrelevant antibody are administered at the same or substantially the same time.

20. a method according to claim 13, wherein the irrelevant antibody is administered up to five hours before administration of the tumour specific antibody.

21. An imaging composition, characterized in that it comprises;
   (i) a tumor specific antibody or a fragment thereof labelled with a paramagnetic element; and
   (ii) a non-tumor reactive antibody labelled with a non-paramagnetic element; in association with a pharmaceutically acceptable carrier or excipient.

22. An imaging composition according to claim 21 wherein the specific antibody and irrelevant antibody are of the same isotype.

23. An imaging composition according to claim 21, wherein the tumour specific antibody and irrelevant antibody are both monoclonal antibodies.

24. An imaging composition according to claim 21, wherein the tumour specific antibody is 17.1 and the non-tumour reactive antibody is Ly 2.1.

* * * * *